(12) United States Patent
Murray (10) Patent No.: US 9,644,103 B2
(45) Date of Patent: May 9, 2017

(54) SINGLE STEP CREOSOTE/BORATE WOOD TREATMENT

(71) Applicant: Stella-Jones Inc., Saint-Laurent (CA)

(72) Inventor: Gordon Murray, North River (CA)

(73) Assignee: Stella-Jones Inc., Saint-Laurent, Quebec (CA)

( * ) Notice: Subject to any disclaimer, the term of this patent is extended or adjusted under 35 U.S.C. 154(b) by 0 days.

(21) Appl. No.: 14/311,803

(22) Filed: Jun. 23, 2014

(65) Prior Publication Data

US 2015/0010768 A1    Jan. 8, 2015

Related U.S. Application Data

(60) Provisional application No. 61/842,625, filed on Jul. 3, 2013, provisional application No. 61/843,308, filed on Jul. 5, 2013.

(51) Int. Cl.
| | | |
|---|---|---|
| C09D 5/14 | (2006.01) |
| B27K 3/08 | (2006.01) |
| A01N 59/14 | (2006.01) |
| A01N 61/02 | (2006.01) |
| C08K 5/55 | (2006.01) |
| C08K 11/00 | (2006.01) |
| B27K 3/46 | (2006.01) |
| B27K 3/50 | (2006.01) |
| C08K 5/13 | (2006.01) |

(52) U.S. Cl.
CPC ............... *C09D 5/14* (2013.01); *A01N 59/14* (2013.01); *A01N 61/02* (2013.01); *B27K 3/08* (2013.01); *B27K 3/46* (2013.01); *B27K 3/50* (2013.01); *C08K 5/13* (2013.01); *C08K 5/55* (2013.01); *C08K 11/00* (2013.01); *Y10T 428/662* (2015.04)

(58) Field of Classification Search
None
See application file for complete search history.

(56) References Cited

U.S. PATENT DOCUMENTS

| | | | |
|---|---|---|---|
| 2,051,486 | A | 10/1934 | Kautter |
| 3,956,100 | A | 5/1976 | Todd |
| 3,960,969 | A | 6/1976 | Greco et al. |
| 4,076,871 | A | 2/1978 | Short et al. |
| 4,234,665 | A | 11/1980 | Johnson |
| 4,461,721 | A * | 7/1984 | Goettsche .............. A01N 59/14 106/18.13 |
| 4,585,795 | A | 4/1986 | Linderborg |
| 4,929,454 | A | 5/1990 | Findlay |
| 5,078,912 | A | 1/1992 | Goettsche et al. |

(Continued)

FOREIGN PATENT DOCUMENTS

GB           249698 A  *  4/1926  ............... B27K 3/44

OTHER PUBLICATIONS

Webb et al. 1958 Cooperative Cerosote Project—XIV:35 years of Field Exposure with Posts. 1995, AWPA Proceedings 91:120.*

(Continued)

*Primary Examiner* — David Turocy
(74) *Attorney, Agent, or Firm* — Foley & Lardner LLP (57) ABSTRACT

Disclosed herein are preservative compositions and methods of using the same for reducing insect and microbial decay in wood. Also disclosed are wooden articles that have been treated with the compositions described herein.

21 Claims, 3 Drawing Sheets

Rueping (Empty Cell) Cycle

A - Initial Air Pressure
B - Fill Cylinder
C - Pressurize Cylinder
D - Pressure Period
E - Release Pressure
F - Expansion Bath
G - Empty Cylinder
H - Final Vacuum
I - Release Vacuum

(56) References Cited

U.S. PATENT DOCUMENTS

| | | | |
|---|---|---|---|
| 5,080,935 A * | 1/1992 | Kelso, Jr. | B27K 1/00 |
| | | | 34/404 |
| 5,098,472 A | 3/1992 | Watkins et al. | |
| 5,104,664 A | 4/1992 | Palmere et al. | |
| 5,246,652 A * | 9/1993 | Hsu | B27N 9/00 |
| | | | 252/607 |
| 5,296,240 A | 3/1994 | Palmere et al. | |
| 5,447,686 A | 9/1995 | Seidner | |
| 5,460,816 A | 10/1995 | Palmere et al. | |
| 5,641,726 A | 6/1997 | Walker | |
| 5,645,828 A | 7/1997 | Palmere et al. | |
| 5,700,841 A | 12/1997 | Walker | |
| 5,709,821 A | 1/1998 | von Bonin et al. | |
| 5,891,921 A | 4/1999 | Walker | |
| 5,958,463 A | 9/1999 | Milne et al. | |
| 6,087,303 A | 7/2000 | Walker | |
| 6,103,387 A | 8/2000 | Yamamoto et al. | |
| 6,426,095 B2 | 7/2002 | Palmere et al. | |
| 6,630,174 B2 | 10/2003 | Palmere et al. | |
| 6,953,201 B1 * | 10/2005 | VanDeMortel | B62K 21/14 |
| | | | 280/276 |
| 6,953,501 B2 | 10/2005 | Kelley et al. | |
| 7,128,778 B2 | 10/2006 | Thompson | |
| 7,597,902 B2 | 10/2009 | Lloyd et al. | |
| 8,709,462 B2 | 4/2014 | Lloyd et al. | |
| 2003/0199655 A1 | 10/2003 | Yurugi et al. | |
| 2004/0028934 A1 | 2/2004 | Preston et al. | |
| 2005/0013939 A1 * | 1/2005 | Vinden | B27K 3/0214 |
| | | | 427/325 |
| 2007/0042161 A1 | 2/2007 | Gibbs | |
| 2007/0151476 A1 | 7/2007 | Humar et al. | |
| 2011/0039031 A1 * | 2/2011 | Cobham | B27K 3/52 |
| | | | 427/427.7 |
| 2012/0148859 A1 | 6/2012 | Cobham | |
| 2012/0171504 A1 * | 7/2012 | Murray | B27K 3/0285 |
| | | | 428/537.1 |
| 2014/0342172 A1 | 11/2014 | Murray | |

OTHER PUBLICATIONS

Langroodi et al., Proceedings of the 107$^{th}$ Annual Meeting of the American Wood Protection Association, May 15-17, 2011 (May 15, 2011), p. 117.

Lebow et al., USDA Forest Service Research Note FPL-RN-0295, 6 pp. (Apr. 2005).

Lesar et al., Performance of Boron-ethanolamine-quaternary Ammonium Based Wood Preservatives Against Leaching, Wood Decay and Blue Stain Fungi, Wood Research, 2008, vol. 53, No. 3, p. 17-26.

Roll, "Wood Preservation Category 4b, Study Guide for Commercial Applicators", Ohio Department of Agriculture—Pesticide Regulation—Certification and Training, Aug. 2003, 3 pps. Access from: <URL: http://pested.osu.edu/documents/CommStudy/4b%20Wood%20Preservation.pdf> p. 28 under E. Pentachlorophenol Solutions.

* cited by examiner

SINGLE STEP CREOSOTE/BORATE WOOD TREATMENT

CROSS-REFERENCE TO RELATED APPLICATIONS

This application is claims the benefit of U.S. Provisional Patent Application 61/842,625, filed on Jul. 3, 2013; and U.S. Provisional Patent Application 61/843,308, filed on Jul. 5, 2013; the entire contents of which are hereby incorporated by reference, for any and all purposes.

BACKGROUND

Wood products have been used as utility poles, railway ties and construction materials in a wide variety of industries. Without proper treatment, wood products deteriorate and are susceptible to weathering, insects (termites, carpenter ants, and beetles), marine borers (mollusks and crustaceans), bacteria and fungi (stains, white rot, soft rot, and brown rot). Wood treatment is required to prevent these problems.

Borates are a broad spectrum insecticide commonly used in the treatment of wood. They have the advantage of being readily diffusible into the interior of wood and exhibit low mammalian toxicity. However, borates have disadvantages in that they are susceptible to leaching and do not adequately protect against soft rot fungi. Exemplary borates include sodium octaborate, sodium tetraborate, sodium pentaborate, boric acid, disodium octaborate tetrahydrate, boron esters and PBA-phenylboronic acid.

Creosote is another chemical commonly used for the treatment of wood. It comprises over 300 different compounds, the majority of which are polycyclic aromatic hydrocarbons. Creosote is a broad spectrum biocide, and, unlike borates, is able to protect against soft rot fungi. However, creosote is unable to penetrate into the interior of heartwood.

A two stage "envelope" treatment process has been developed to address the problems associated with treatment by borates or creosote individually. The wood is first immersed in a borate composition for about six weeks, thereby allowing the borate to diffuse throughout the wood. This first step is followed by treatment with creosote to form a hydrophobic envelope around the wood. The creosote envelope prevents leaching of the borate and is active against soft rot fungi. As such, the envelope treatment is highly effective in reducing and/or preventing wood deterioration due to microorganisms.

However, the two step envelope treatment also suffers from serious drawbacks. First, it requires that the wood be dry. More serious is the six week borate treatment, which is extremely time consuming and inefficient. Finally, extra handling and equipment is required to carry out the process. As such, new methods of applying the envelope treatment that require less time and handling and allow for the use of wood with a higher moisture content are urgently needed.

SUMMARY

Disclosed herein is a one step process for treating wood with one or more borates and creosote. The experiments described herein show that both creosote and boron from the one or more borates penetrated railway ties treated with the disclosed one step process. Penetration of creosote stopped at the heartwood and boron diffused beyond the heartwood. Boron penetration is shown colorimetrically using curcumin solution and confirmed by Induced Coupled Plasma Emission Analysis. Penetration of boron into treated railway ties occurs in couple of hours and thereby eliminates the six week borate treatment step. The disclosed one step process can also be used to treat wood with higher moisture content than is compatible with the prior two step process (Examples 7 and 8).

One embodiment of the present technology is a method of treating wood, where the method comprises the steps of:
  a) immersing the wood in a treatment composition comprising i) a $C_1$-$C_6$ monoalkanolamine complex of a borate and ii) creosote; and
  b) exposing the immersed wood from step a) to conditions which cause the release of boron from the $C_1$-$C_6$ monoalkanolamine complex of a borate and which cause the boron to migrate into the interior of the wood.

Another embodiment of the present technology is a method of treating wood, where the method comprises the steps of:
  a) immersing the wood in a treatment composition comprising i) a monoalkanolamine complex of DOT and/or boric acid and ii) creosote;
  b) exposing the immersed wood from step a) to conditions which cause the release of boron from the monoalkanolamine complex of DOT and/or boric acid and which cause the boron to migrate into the interior of the wood.

Another embodiment of the present technology is a method of treating wood, where the method comprises the steps of:
  a) immersing the wood in a treatment composition comprising i) an alkanolamine complex of borate and ii) creosote; and
  b) exposing the immersed wood to a temperature of between 160-240° F. and a pressure of 100-160 pounds per square inch (psi) (preferably 190-210° F. and a pressure of 130-160 psi). The duration of the exposure is at least ten minutes. Alternatively, the duration of the exposure is from ten minutes to ten hours. In yet another alternative, the duration of the exposure is from 20 minutes to 5 hours.

In some embodiments, the method for treating wood is used for reducing insect and microbial decay in the wood. Another embodiment of the present technology is a composition comprising: 1) between 3% w/w to 10% w/w of an alkanolamine complex of borate; and 2) between 90% w/w and 97% w/w creosote.

Yet another embodiment of the present technology is an article, where the article is wood coated with or immersed in a composition comprising: 1) between 3% w/w to 10% w/w of an alkanolamine complex of borate (e.g., monoethanolamine complex of borate); and 2) between 90% w/w and 97% w/w creosote.

Another embodiment of the present technology is an article, wherein the article is wood prepared according to any of the methods described herein. In some embodiments, the wood is treated with creosote comprising heavy bunker C fuel oil. In some embodiments, the creosote may comprise about 50% w/w heavy bunker C fuel oil.

Another embodiment of the present technology is an article, wherein the article is wood comprising a composition, and wherein the composition comprises i) a alkanolamine complex of a borate and ii) creosote.

Another embodiment of the present technology is a composition comprising i) a alkanolamine complex of a borate and ii) creosote.

In some embodiments of the article or the composition, the alkanolamine comprises a monoalkanolamine. In some embodiments of the article or the composition, the monoalkanolamine comprises a $C_1$-$C_6$ monoalkanolamine. In some embodiments of the article or the composition, the $C_1$-$C_6$ monoalkanolamine comprises ethanolamine.

In some embodiments of the article or the composition, the borate comprises boric acid. In some embodiments of the article or the composition, the borate comprises DOT. In some embodiments of the article or the composition, the borate comprises boric acid and DOT. In some embodiments of the article or the composition, the borate comprises an approximately 50/50 mixture of boric acid and DOT.

In some embodiments of the article or the composition, the alkanolamine complex of a borate comprises a monoester and/or a diester and/or a triester of the borate. In some embodiments of the article or the composition, the alkanolamine complex further comprises unreacted borate.

In some embodiments of the article or the composition, the creosote comprises heavy bunker C fuel oil. In some embodiments of the article or the composition, the creosote comprises about 50% w/w heavy bunker C fuel oil.

DETAILED DESCRIPTION

The present application is directed to a one step process for treating wood. In some embodiments, the method is used to prevent or reduce insect or microbial decay in the wood. The wood is coated or immersed in a treatment composition comprising an alkanolamine complex of borate and creosote. The coated or immersed wood is then exposed to conditions that are suitable for causing release of boron from the alkanolamine/borate complex and to cause the released boron to migrate into the interior of the wood.

Creosote is a distillate obtained from tars produced from the carbonization of bituminous coal and is a mixture of over three hundred chemicals such as polycyclic aromatic hydrocarbons (PAHs), phenol and cresols created by high temperature treatment of coal. Creosote is commonly used as a biocide to coat wood and protect it from soft rot fungi and to prevent leaching of boron from the interior.

In some embodiments, the term creosote, as used herein can be substantially pure creosote or creosote that is diluted with "heavy bunker C fuel oil" as per specifications set by the American Wood Protection Association (AWPA). In some embodiments, the "creosote described herein is diluted with 10% w/w, 20% w/w, 30% w/w, 40% w/w, 50% w/w, 60% w/w, 70% w/w, 80% w/w, 90% w/w, or a percentage between any two of these values, of heavy bunker C fuel oil. In some embodiments, the creosote described herein is diluted with about 40% w/w to about 60% of heavy bunker C fuel oil. In some embodiments, the creosote described herein is diluted with about 50% of heavy bunker C fuel oil.

In some embodiments of any of the methods described herein, the creosote may comprises heavy bunker C fuel oil. In some embodiments of any of the compositions or solutions described herein, the creosote may comprises heavy bunker C fuel oil. In some embodiments of any of the articles such as wood described herein, the creosote may comprises heavy bunker C fuel oil. In some embodiments, the creosote may comprise about 50% w/w heavy bunker C fuel oil.

As used herein, the term "borate" refers to a borate compound containing oxoanions of boron in a +3 oxidation state. The simplest borate ion, $BO_3^{3-}$, and its acidic counterpart, boric acid $B(OH)_3$, have trigonal planar structures. Other borates include trigonal $BO_3$ or tetrahedral $BO_4$ structural units, sharing oxygen atoms. A number of polymeric borate ions are known. They may be made by reacting $B(OH)_3$ or $B_2O_3$ with metal oxides. Examples include: diborate $B_2O_5^{4-}$ (e.g., $Mg_2B_2O_5$), triborate $B_3O_7^{5-}$ (e.g., $CaAlB_3O_7$), tetraborate $B_4O_9^{6-}$ (e.g., sodium tetraborate $Na_2B_4O_7 \cdot 10H_2O$), pentaborate $B_5O_6(OH)_4^-$ (e.g., sodium pentaborate $Na[B_5O_6(OH)_4] \cdot 3H_2O$), and octaborate (e.g., disodium octaborate tetrahydrate, "DOT" or Tim-Bor, $Na_2B_8O_{13} \cdot 4H_2O$). In some embodiments, the borate used herein is boric acid. In some embodiments, the borate used herein is DOT.

In some embodiments, the borate used herein is a mixture of borates, such as boric acid and a polymeric borate such as DOT, where the mixture includes boric acid in about 5% w/w, 10% w/w, 20% w/w, 30% w/w, 40% w/w, 50% w/w, 60% w/w, 70% w/w, 80% w/w, 90% w/w relative to the mixture of borates, or an amount in between any two of these percentages, and DOT in about 5% w/w, 10% w/w, 20% w/w, 30% w/w, 40% w/w, 50% w/w, 60% w/w, 70% w/w, 80% w/w, 90% w/w relative to the mixture of borates, or an amount in between any two of these percentages. In some embodiments, the borate includes about 40% w/w boric acid and about 60% w/w DOT. In some embodiments, the borate includes about 50% w/w boric acid and about 50% w/w DOT. In some embodiments, the borate includes about 60% w/w boric acid and about 40% w/w DOT.

In some embodiments, the borate used herein is a mixture of two or more polymeric borates, where each polymeric borates is included in about 5% w/w, 10% w/w, 20% w/w, 30% w/w, 40% w/w, 50% w/w, 60% w/w, 70% w/w, 80% w/w, 90% w/w relative to the mixture of polymeric borates, or an amount in between any two of these percentages. As used herein the term borate can further mean a boric equivalent.

As used herein, the term "alkanolamine" refers to $C_1$-$C_{20}$ branched or unbranched alkylene groups substituted with amino and hydroxy substituents (e.g., monoethanolamine "MEA", diethanolamine "DEA," triethanolamine "TEA" or combinations thereof). In some embodiments, the alkanolamine refers to $C_1$-$C_{12}$ branched or unbranched alkylene groups substituted with amino and hydroxy substituents. In some embodiments, the alkanolamine refers to $C_1$-$C_6$ branched or unbranched alkylene groups substituted with amino and hydroxy substituents. In some embodiments, the alkylene group is interrupted with one or more —O— groups (e.g., the alkylene group includes (—CH$_2$CH$_2$—O)$_n$ linkages where n is 1, 2, 3, 4, 5, 6, 7, 8, 9 or 10). The term "alkylene," as used herein, is a divalent alkyl group.

In some embodiments, the alkanolamine is a mixture of MEA in about 5% w/w, 10% w/w, 20% w/w, 30% w/w, 40% w/w, 50% w/w, 60% w/w, 70% w/w, 80% w/w, 90% w/w relative to the mixture of alkanolamines, or an amount in between any two of these percentages, and DEA in about 5% w/w, 10% w/w, 20% w/w, 30% w/w, 40% w/w, 50% w/w, 60% w/w, 70% w/w, 80% w/w, 90% w/w relative to the "mixture" of alkanolamines, or an amount in between any two of these percentages. In some embodiments, the alkanolamine mixture further includes TEA, or TEA is used to replace either MEA or DEA, where the TEA is used in about 5% w/w, 10% w/w, 20% w/w, 30% w/w, 40% w/w, 50% w/w, 60% w/w, 70% w/w, 80% w/w, 90% w/w relative to the mixture of alkanolamines, or in an amount between any two of these percentages.

The "alkanolamine/borate complex," also described herein as an "alkanolamine complex of a borate," refers to a mixture comprising one or more alkanolamines and one or more borates. In some embodiments, the alkanolamine/borate complex may include a monoester and/or diester and/or triester as shown and described in Schemes 1 and 2 below. In some embodiments, the alkanolamine/borate complex may include unreacted borate (e.g., unreacted boric acid and/or polyborates such as DOT, as shown in Schemes 1 or 2). In some embodiments, the alkanolamine/borate complex may include a monoester and/or diester and/or triester and/or unreacted borate. In some embodiments, the alkanolamine/borate complex includes less than one molar equivalent of alkanolamine relative to borate and, in such embodiments, generally includes unreacted borate.

Scheme 1-Formation of an alkanolamine/borate complex from boric acid

Scheme 2-Formation of an alkanolamine/borate complex from polymeric borate ions such as DOT In Schemes 1 and 2 R$^A$ is a C$_1$-C$_{20}$ branched or unbranched alkylene linker, optionally interrupted with one or more —O— groups (e.g., the alkylene group includes (—CH$_2$CH$_2$—O)$_n$ linkages where n is 1, 2, 3, 4, 5, 6, 7, 8, 9 or 10).

The alkanolamine/borate complex may further comprise a solvent. As used herein, the term "solvent" refers to C$_1$-C$_{20}$ branched or unbranched alcohols (e.g., ethanol, isopropanol, glycerol or propylene glycol, etc.) In some embodiments, the solvent refers to a C$_1$-C$_{12}$ alcohol. In some embodiments, the solvent refers to a C$_1$-C$_6$ alcohol. In some embodiments, C$_1$-C$_{20}$ branched or unbranched alcohol includes one or more (—CH$_2$CH$_2$—O)$_n$ linkages where n is 1, 2, 3, 4, 5, 6, 7, 8, 9 or 10). In some embodiments, the solvent is added to the alkanolamine/borate complex in about in about 1% w/w, 2% w/w, 5% w/w, 10% w/w, 20% w/w, 30% w/w, 40% w/w, 50% w/w, 60% w/w, 70% w/w, 80% w/w, 90% w/w relative to the weight percentage of the alkanolamine/borate complex.

In some embodiments, the hydroxyl group of the alkanolamine (e.g., ethanolamine, diethanolamine or triethanolamine) and/or the hydroxyl group of the solvent (e.g., ethanol, glycerol or propylene glycol) may react with the borate to form an ester of the borate such that up to 2% w/w, up to 5% w/w, up to 10% w/w, up to 15% w/w, up to 20% w/w, up to 25% w/w, up to 30% w/w, up to 40% w/w, up to 50% w/w, up to 60% w/w, up to 70% w/w, up to 80% w/w, up to 90% w/w, up to 100% w/w of the borate is converted to an ester, or an amount in between any two of these percentages. In some embodiments, the ester of the borate includes a monoester of the borate, a diester of the borate, a triester of the borate, or a mixture of two or more of the foregoing.

The alkanolamine/borate complex may be a monoalkanolamine/borate complex. The ethanolamine complex, for example, is preferred and is referred to herein as the "ME Ester," although this "ME ester can include monoester and/or diester and/or trimester and/or unreacted borate. In some embodiments, the borate of the monoalkanolamine/borate complex is DOT and/or boric acid.

In some embodiments, the alkanolamine/borate complex may be a C$_2$-C$_6$ monoalkanolamine/borate complex, The $C_2$-$C_6$ monoalkanolamine complex of a borate can include a salt, a monoester of the borate, e.g., boric acid or DOT, a diester of the borate, e.g., boric acid or DOT, a triester of the borate, e.g., boric acid or DOT or a mixture of two or more of the foregoing. Preferably, the $C_2$-$C_6$ monoalkanolamine ester is a monoalkanolamine complex of DOT and/or boric acid.

The $C_2$-$C_6$ monoalkanolamine complex is prepared by mixing $C_2$-$C_6$ monoalkanolamine in an aqueous composition of borate and allowing the $C_2$-$C_6$ monoalkanolamine to react with the borate. In some embodiments, the $C_2$-$C_6$ monoalkanolamine is monoethanolamine.

The concentration of alkanolamine (e.g., $C_2$-$C_6$ monoalkanolamine) in the reaction mixture to form the alkanolamine/borate complex can be 5-43% w/w relative to the weight % of the alkanolamine/borate complex reaction mixture; the concentration of water in the reaction mixture can be 2-27% w/w relative to the weight % of the alkanolamine/borate complex reaction mixture; and the concentration of borate (e.g., boric acid and/or DOT) in the reaction mixture can be 10-95% w/w (e.g., 10% w/w, 20% w/w, 30% w/w, 40% w/w, 50% w/w, 60% w/w, 40-60% w/w, 70% w/w, 80% w/w, 90% w/w, or an amount between any two of these percentages) relative to the weight % of the alkanolamine/borate complex reaction mixture.

Alternatively, the concentration of alkanolamine (e.g., $C_2$-$C_6$ monoalkanolamine) in the reaction mixture is 28-38% w/w; the concentration of water in the reaction mixture is 12-22% w/w; and the concentration of borate in the reaction mixture is 45-55% w/w relative to the weight % of the alkanolamine/borate complex reaction mixture. In yet another alternative, the concentration of alkanolamine (e.g., $C_2$-$C_6$ monoalkanolamine) in the reaction mixture is 31-35% w/w; the concentration of water in the reaction mixture is 15-19% w/w; and the concentration of borate in the reaction mixture is 48-52% w/w relative to the weight % of the alkanolamine/borate complex reaction mixture.

In yet another alternative, the concentration of alkanolamine (e.g., $C_2$-$C_6$ monoalkanolamine) in the reaction mixture is 10-30% w/w; the concentration of water in the reaction mixture is 1-20% w/w; and the concentration of borate in the reaction mixture is 53-85% w/w relative to the weight % of the alkanolamine/borate complex reaction mixture. For example, the concentration of alkanolamine (e.g., $C_2$-$C_6$ monoalkanolamine) in the reaction mixture may be about 25% w/w; the concentration of water in the reaction mixture may be about 15% w/w; and the concentration of borate in the reaction mixture may be about 60% w/w relative to the weight % of the alkanolamine/borate complex reaction mixture. Alternatively, the concentration of alkanolamine (e.g., $C_2$-$C_6$ monoalkanolamine) in the reaction mixture may be about 16% w/w; the concentration of water in the reaction mixture may be about 4% w/w; and the concentration of borate in the reaction mixture may be about 80% w/w relative to the weight % of the alkanolamine/borate complex reaction mixture.

The quantity of alkanolamine (e.g., $C_2$-$C_6$ monoalkanolamine or monoethanolamine) in the reaction mixture relative to borate can be adjusted upward, resulting in greater amounts of di and triester relative to the alkanolamine/boronate complex; or downwards, resulting in lesser amounts of di and triester. Because the reaction is exothermic, the formation of a complex between the borate and an alkanolamine is preferably carried out with cooling. Because water is preferably substantially absent from the treatment solution used in the pressure impregnation step, it is advantageous to evaporate away as much water as possible from the heat that is generated from the exotherm that occurs during the formation of a complex between the borate and an alkanolamine.

The reaction product of the alkanolamine (e.g., $C_2$-$C_6$ monoalkanolamine or monoethanolamine) is then blended with creosote to form the treatment composition for the pressure impregnation. The temperature of this blending step is not critical, however, the temperature is typically elevated in order to decrease the viscosity of the creosote and thereby facilitate the blending and to remove any remaining water present in the borate complex composition. As such, the temperature and period of time during which the elevated temperature is maintained is adjusted so that the blend is homogeneously mixed and substantially all water has been removed through evaporation (e.g., greater 95%. 98% or 99% w/w free of water). Temperatures between 160-200° F. are commonly used. The final concentration of alkanolamine/borate complex in the treatment composition is from 10-3% w/w; and the final concentration of creosote in the treatment composition from 90-97% w/w. Alternatively, the final concentration of alkanolamine/borate complex in the treatment composition is from 5-3% w/w; and the final concentration of creosote in the treatment composition is from 95-97% w/w.

To carry out the disclosed processes, the wood being treated to reduce insect and/or microbial decay is immersed in the treatment composition and subjected to conditions that cause boron to be released from the Alkanolamine/borate complex and to migrate into the interior of the wood. The transfer of the boron from the creosote into the wood is as elemental boron which reacts quickly to form the boric acid equivalent ($B_2O_3$) found in the AWPA texts. This chemical is exchanged back and forth as the material enters the wood. The boron moves from the composition in response to the higher moisture content in the core of the wood and the higher charge associated with heartwood. It moves primarily as B2O3 but quickly reacts with the numerous wood sugars, tannins, acids and natural decay resistant chemicals such as Tropolones and Stilbenes to form numerous complexes.

One great advantage of the disclosed process is that conditions commonly used in the prior two step process to treat wood with creosote alone can be used in the disclosed one step process. For example, pressure impregnation, a process commonly used to coat wood with creosote in the prior two step process, is suitable for use in the disclosed one step process. Whereas pressure impregnation is used in the prior two step process to apply an envelope coating of creosote to the wood being treated, in the disclosed one step process, pressure impregnation is used to both apply the envelope coating of creosote and to cause the Alkanolamine/borate complex to decompose and release boron and to cause the released boron to migrate into the interior of the wood.

Pressure impregnation refers to subjecting wood that is immersed in the treatment composition to elevated temperature and pressure for a period of time sufficient to achieve release of boron and migration of the released boron throughout the interior of the wood to thereby achieve a sufficient concentration of boron to reduce insect and microbial degradation. Suitable concentrations of boron in the interior of the wood are at least 0.05 pounds per cubic foot (pcf) and preferably at least 0.11 pcf. The precise temperature and pressure can vary according to the thickness and type of wood and length of the treatment time. The person of ordinary skill will be able to determine suitable parameters to achieve a suitable concentration and distribution of boron by monitoring the migration of the boron throughout the interior of the wood by, for example, atomic absorption and inductively couple argon plasma Screening can be accomplished, for example, by using the AWPA boron stain to confirm presence or absence of boron in the wood as a rapid screening mechanism. (AWPA A3-08-17, 2010) and adjusting the parameters accordingly. Commonly used conditions for the pressure impregnation include a pressure of between 100-160 psi and a temperature of between 160-240° F. Alternative conditions include a pressure of between 130-160 psi and a temperature of between 190-210° F. Treatment time is at least 10 minutes, 10 minutes to 10 hours or 20 minutes to five hours.

The pressure impregnation is carried out in a pressure vessel. Exemplary pressure vessels include cylindrical retorts that are 5' to 8' in diameter and of lengths up to 200' which allow for the uniform application of temperature, air and fluid pressure and vacuum. They consist of a long cylindrical tube, certified as a pressure vessel which can handle pressures of at least 250 psi, doors must be rated for the same pressure to allow for entry and exit of the wood. The wood is placed into the retort on small railcars or trams. A working solution tank is used to fill the cylinder with the wood present under various pressure and temperature conditions. The retort holds the wood immersed in the chosen treating composition and allows for control of pressure through fluid pumps and air compressors, temperature with heat exchange coils and vacuum with liquid ring pumps. These systems are designed to give uniform conditions through the volume of the retort so that all areas of the wood are subjected to equal temperature and pressure conditions. Pressure vessels are commercially available from any large steel fabrication facility. Regulations for their design vary from state to state and country to country.

Following pressure impregnation, the wood is separated from the treatment composition. When the process is carried out in a pressure vessel, this is typically accomplished by releasing the pressure and pumping the treatment composition out of the pressure vessel. However, any other suitable means of separating a solid from a liquid can be used, including filtration or centrifugation.

In one embodiment, the cylinder is pressurized with air before it is filled with the treatment composition. This step is referred to herein as "Pretreatment Pressurization". Suitable pressures range from atmospheric pressure to 75 psi. Alternatively, the pressure ranges from 0-25 psi. The Pretreatment Pressurization typically lasts from 10 minutes to 10 hours. Alternatively, the Pretreatment Pressurization lasts from 10 minutes to 3 hours. In another alternative, the Pretreatment Pressurization lasts from 20 minutes to one hour. Following Pretreatment Pressurization, the pressure is maintained while the wood is immersed in the treatment composition for pressure impregnation.

Following the pressure impregnation and separation of the wood from the treatment composition, the wood can be subjected to an expansion bath. An expansion bath is used to minimize leaching and bleeding after treatment and to remove excess preservative from the surface of the wood. Leaching refers to precipitation of the preservative on the surface of the wood from where it is often transported in rain/snow away from the wood. Bleeding refers to the movement of preservative resulting from the change of moisture gradient (wet centers), physically moving the preservative to the surface of the material. Subjecting the wood to an expansion bath refers to immersing the wood in a higher temperature oil and subjecting the oil and immersed wood to elevated temperatures, typically a temperature higher than what was used for the pressure impregnation, typically about 10-40° F. higher; alternatively from 10-20° F. higher. Temperatures of 220-250° F. are commonly used, alternatively from 220-230° F. The duration of exposure is at least 30 minutes, alternatively from 0.5 to five hours. In another alternative, the duration is from one to two hours. Examples of suitable high temperature oils include the oils used in the pressure impregnation. For example, the oil mixture used for the pressure impregnation can be conveniently used for the expansion by adjusting the temperature upwards. When the expansion bath treatment is completed, the oil is separated from the wood. When the process is carried out in a pressure cylinder, the oil is typically pumped out of the apparatus. Other suitable separation methods can also be used, e.g., filtration. The separation of the oil from the wood is considered herein to be part of the expansion bath.

The expansion bath treatment and separation of the oil from the treated wood is typically followed by vacuum treatment to remove residual liquid. The final vacuum is carried out at least 10 inches of mercury and typically between 15 and 40 inches, more commonly between 20 and 28 inches of mercury. The duration of the vacuum treatment is for at least 15 minutes, alternatively from 0.5 to ten hours and in another alternative from 0.5 to five hours and in another alternative from 0.5 to two hours.

Figure 1:
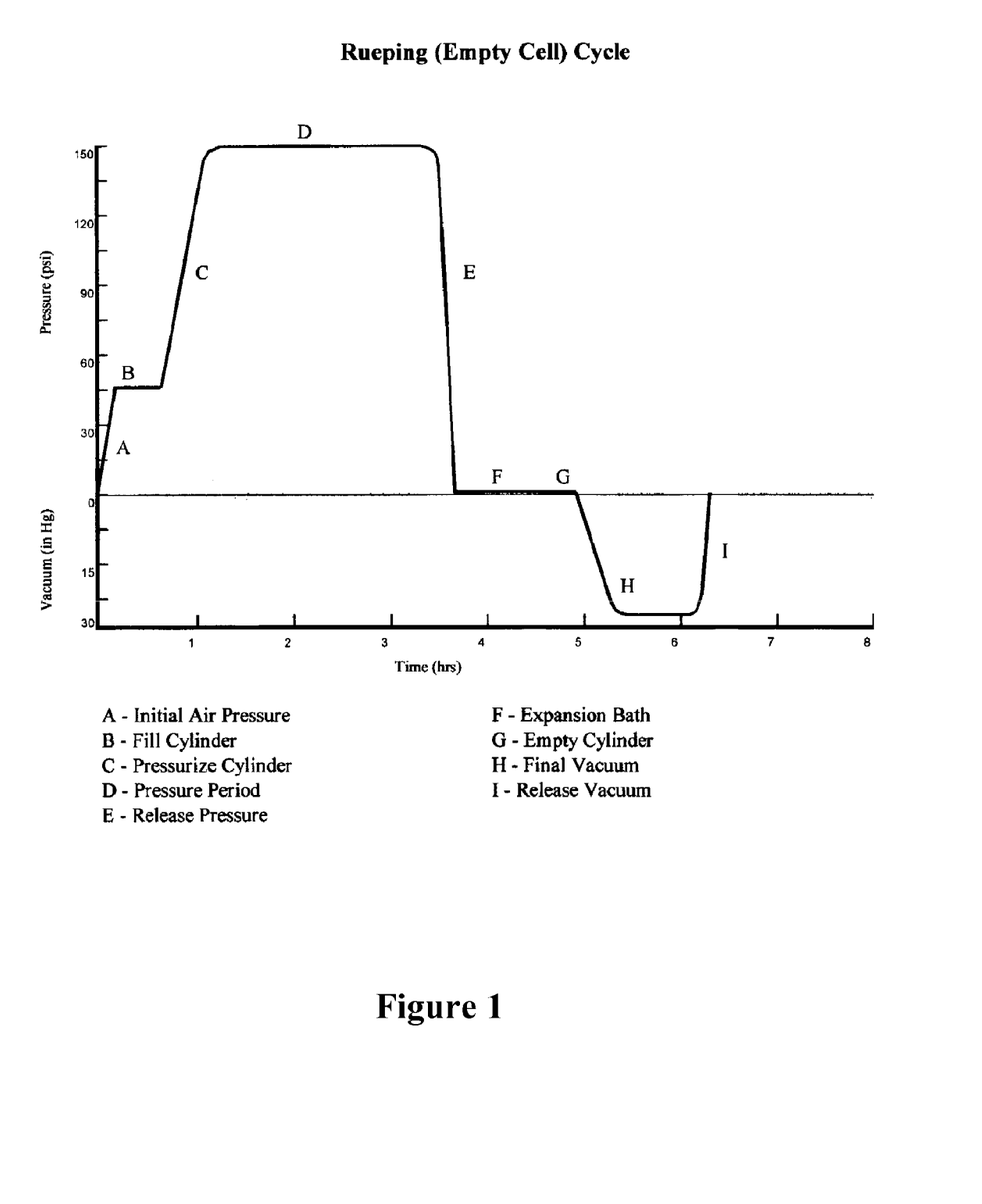
FIG. 1 is a schematic showing the pressure in pounds per square inch or vacuum in inches mercury which are used in the Ruepig Cycle versus time.
Figure 2:
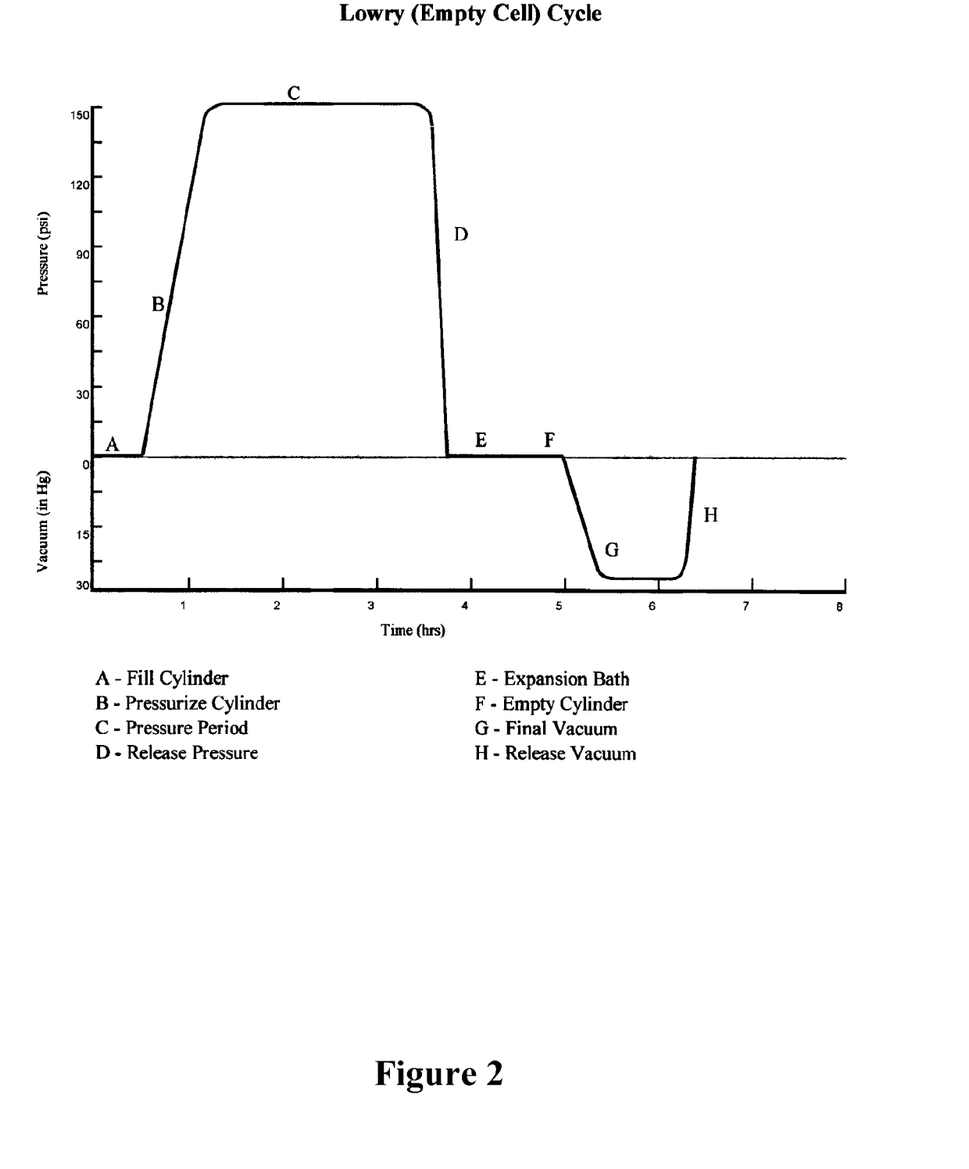
FIG. 2 is a schematic showing the pressure in pounds per square inch or vacuum in inches mercury which are used in the Lowry Cycle versus time.

The Lowry Process and Ruepig Process are well known in the art for applying an envelope coating of creosote to wood. Both of the processes are suitable for the disclosed one step wood treatment process for impregnating wood with boron and envelope coating the wood with creosote. The pressure and vacuum conditions used over time for both of these processes are shown schematically in FIGS. 1 and 2. The Lowry Process and Ruepig Process are described more fully in the AWPA (AWPA T1-10, 2010).

The prior two step process requires the use of wood that is dry, i.e., has a moisture content between 20-40% w/w. Because the moisture content of most wood is greater than 20-40% w/w, a drying step is often necessary before the prior two step process can be employed. Moisture can be removed from wood by, for example, immersing the wood in oil at elevated temperature under vacuum, e.g., at around 180° F. at 24 inches Hg. While the disclosed process can readily treat "dry" wood, one advantage of the disclosed one step process compared with the prior two step process is that wood does not need to be rigorously dried in order to be treated by the disclosed one step process. Specifically, the disclosed process can also be used to treat wood that is "semi dry" (i.e., a moisture content of between 40-70% w/w) and "wet" (i.e., a moisture content above 70% w/w). Moreover, the disclosed process is not limited to any particular type of wood. Examples of wood that can be used in the disclosed process include, but are not limited to, Pine (e.g., Red Pine, Jack Pine, Southern Yellow Pine, Lodgepole Pine), Fir (e.g., Douglas Fir), Western Red Cedar, Spruce, Eastern and Western Hemlock and hardwoods (e.g., Oak).

Wood is commonly in the form of a cant when treated according to the disclosed process. A cant is the square section of timber that follows the removal of the outer bark.

The present compositions and methods are illustrated by the following examples, which are not intended to be limiting in any way.

EXEMPLIFICATION

Example 1

Preparation of a Borate/Creosote Composition

All boron sources used were AWPA 2010 compatible and expressed as Boric Acid Equivalent (BAE) which is $B_2O_3$.

The objective was to determine whether Tim-Bor (disodium octaborate tetrahydrate or D.O.T.) could be dissolved in creosote, or a co-solvent which could then be added to creosote.

Treatments: Monoethanolamine Borate Ester
    Monoethanolamine (non-ester)
    creosote
    biodiesel
Control: water
Replications: Each treatment was replicated three times.

Ten grams of Tim-Bor was added to round bottomed flasks containing 100 mL of each treatment. The flasks were then attached to a rotary evaporator (Büchi R-124) for 1 hour at 60 rpm and a temperature of 80° C.

All results were qualitative in nature, did the Tim-Bor dissolve in the treatment or not? The basis of this was, if the composition was free of clumps or clouds then the Tim-Bor was considered to be dissolved. The flasks were then capped and allowed to cool for 24 hours at which time the composition was checked to ensure the Tim-Bor remained dissolved in the solvent.

The only treatment to dissolve the Tim-Bor was the monoethanolamine borate ester. Through further testing it was determined that up to 40 g Tim-Bor could be dissolved in 100 mL monoethanolamine borate ester (MBE) using the above described rotary evaporator method.

Example 2

Effect of Varying Amounts and Types of Borate Preservatives Added to Creosote on Diffusion of Borate into Wood Treated with the Disclosed One Stage Process The objective was to examine the effect of varying amounts and types of borate preservatives added to creosote on diffusion of borate into wood treated with one stage creosote/borate in a mini-pilot wood treating plant.

Treatments: 1% Tim-Bor
    1% Tim-Bor/monoethanolamine borate ester
    1% monoethanolamine borate ester
    5% Tim-Bor
    5% Tim-Bor/monoethanolamine borate ester
    5% monoethanolamine borate ester
Control: 100% creosote Twenty-eight hardwood stakes were cut measuring 2 in×2 in×12 in each. 2 L of each preservative treatment mixture was needed per charge in the mini-pilot wood treating plant (Canadian Erectors Manufacturing Ltd.). The wood stakes were treated using the Lowry process with a steam coil heater operating at 180° F. during the initial bath and pressure cycle. Each charge took approximately 6 hours. Following each charge, 2 of the stakes were wrapped in plastic wrap and 2 stakes were left unwrapped. All stakes were placed in storage in a covered bin in an unheated building. The stakes were tested for borate diffusion at 3 and 6 weeks using AWPA method A3-08 (Method for determining penetration of boron-containing preservatives and fire retardants). At the end of each sampling period, a wrapped and unwrapped stake from each treatment was cut in half and the cut edge was sprayed with the indicator solution to determine borate diffusion.

After 3 weeks of storage the stakes were tested for boron diffusion. Following the application of the indicator solutions (AWPA method A3-08), with the exception of control, it was observed that each sample turned an orange/red color, which indicates that borate diffused through the wood. The stakes were tested again at 6 weeks with the same diffusion results.

The indicator solutions test showed that neither the color intensity nor depth of boron diffusion differed between the 5% Tim-Bor/MBE and the 5% MBE treatments. The ICP results indicated only a slight increase in B concentration in the treated wood. The concentration of boric acid in the monoethanolamine was increased to assess whether the same BAE (boric acid equivalent) could be achieved in the treated wood. In fact, it proved possible to increase the concentration of boric acid in the MBE from 30% to 52%.

A stabilizer was required to prevent the boron from coming out of solution. To adopt more environmentally sensitive technologies, biodiesel was chosen as the stabilizer. Biodiesel is already being used as a component of the carrier oil within the oil-borne preservative wood treating system and therefore its use would not require any equipment upgrades. Odor suppression is a side benefit of this project.

Example 3

Amount of Stabilizer Required to Prevent from Coming Out of Solution

Experiment were undertaken to determine the minimum amount of stabilizer, in the form of biodiesel, that needs to be added to the highly concentrated MBE (52% boric acid) to prevent boron from coming out of solution and forming deposits.

Treatments: 50% monoethanolamine borate ester/50% biodiesel
    75% monoethanolamine borate ester/25% biodiesel
    85% monoethanolamine borate ester/15% biodiesel
    90% monoethanolamine borate ester/10% biodiesel
Control: 100% monoethanolamine borate ester (52%)

Fifteen 3.8 L metal containers were each half filled with the appropriate treatment or control. The contents were agitated by stirring and the composition was allowed to coat the sides of the cans. This was to mimic the handling of drums prior to transport and storage. The containers were then allowed to sit undisturbed for a period of one month. The container contents were checked weekly and observations were made on the occurrence of boron deposits.

After 1 month, all metal containers containing MBE/biodiesel mixtures were absent of boron deposits. It was determined that biodiesel was an effective stabilizer for the concentrated MBE.

An added feature that became apparent from adding biodiesel to the concentrated MBE was the decrease in viscosity of the mixture as compared to the ester alone. The concentrated MBE is very viscous and can be difficult to work with in the field. It was determined through employee survey that the 85% MBE/15% biodiesel mixture was most desirable for ease of handling and performance pertaining to equipment (i.e. reduced number and size of emulsions which clog equipment lines). The biodiesel is added to the concentrated MBE by the manufacturer before shipping and therefore does not add an additional step to the procedure at the wood treating plant level. Though we have not tried them at the full production level we are as high as 69% boric acid with 10% biodiesel.

Example 4

Efficacy Testing of Wood Treated by the Disclosed Process

Given the time constraints the proposed treating solutions were subjected to testing by the ASTM test fungi in Petri dishes. This allows for the most rapid determination of efficacy in the ideal growth conditions for the fungi of concern. Agar plate tests using the specified test fungal cultures was then performed on those MBE compositions selected for delivery of the boron. The certified cultures were obtained from the American Type Culture Collection (ATTC) and propagated as per the product information sheets:

*Irpex lacteus*: ATTC number 11245, yeast medium Difco 0712 (ATTC medium no. 200)
*Neolentius lepideus*: ATTC number 12653, YM agar Difco 0712 (ATTC medium no. 200)
*Postia poria*: ATTC number 11538, YM agar Difco 0712 (ATTC medium no. 200)
*Pleurotus ostreatus*: ATTC number 32237, YM agar Difco 0712 (ATTC medium no. 200)
*Trametes versicolor*: ATTC number 42462, Hagem's-Modess medium (ATTC medium no. 479)
*Gleoephyllum trabeum*: ATTC number 11539, Potato Dextrose Agar with 0.5% yeast extract (ATCC medium no. 337)

Each plate was then inoculated in a flame induced sterile environment with a 5 mm diameter agar plug fungal colony of those fungi listed (Hill and Stratton, 1991). Plates subsequently received surface application, rather than an incorporation method, of the 0.5 ml and 1 ml of the new blend compositions from the supplier at concentrations of 5 and 8%, creosote with the 5 and 8% blends and controls with only the fungal colony. This was in keeping with the poisoned agar technique used by Stratton, 1989 and modified by Hill and Stratton in 1991. The plates were incubated for 14 days at 30 C and the presence or absence of fungal growth was noted and measured.

The results of agar plate testing are shown in Table 1 and 2. Primary concern was with boron efficacy and the agar used represents the ideal media for the growth of fungi in an environment much more hospitable than any found in nature. The growth of fungi was completely inhibited at all concentrations and additions of the proposed boron esters and blends. Some plates showed minor cross contamination of bacterial colonies at the 0.5 ml addition. The spotting was present randomly, over the surface of the plates on both strengths of boron esters. Growth was not related to the fungal colony. Controls showed complete coverage of the plate.

TABLE 1

Agar Plate Testing with MBE compositions and MBE/creosote blends and 5 and 8% compositions and blends with creosote with controls—1 ml.

| Fungi | Replications | Control | MBE Blends 5% | MBE Blends 8% | MBE/Creo blend 5% | MBE/Creo blend 8% |
|---|---|---|---|---|---|---|
| 11245 | 7 | FPG | NG | NG | NG | NG |
| 12653 | 7 | FPG | NG | NG | NG | NG |
| 11538 | 7 | FPG | NG | NG | NG | NG |
| 32237 | 7 | 95% | NG | NG | NG | NG |
| 42462 | 7 | FPG | NG | NG | NG | NG |
| 11539 | 7 | FPG | NG | NG | NG | NG |

FPG—Full growth of Fungi on Plate Agar
NG—No Growth of Fungi on Plate Agar

TABLE 2

Agar Plate Testing with MBE compositions and MBE/creosote blends and 5 and 8% compositions and blends with creosote with controls—0.5 ml.

| Fungi | Replications | Control | Boron Ester Blends 5% | Boron Ester Blends 8% | Boron Ester/Creo 5% | Boron Ester/Creo 8% |
|---|---|---|---|---|---|---|
| 11245 | 7 | FPG | NG | NG | NG | NG |
| 12653 | 7 | FPG | NG | NG | NG | NG |
| 11538 | 7 | FPG | NG | NG | NG | NG |
| 32237 | 7 | 95% | NG | NG | NG | NG |
| 42462 | 7 | FPG | NG | NG | NG | NG |
| 11539 | 7 | FPG | NG | NG | NG | NG |

Example 5

Soil Block Culture of Wood Treated with the Disclosed One Step Process

Blocks (14-19 mm) hardwood were tested at various retentions of MBE/Creosote in a 5 step retention series. This allowed for the exposure of the treated blocks to recognized destructive species of fungi outlined above. These blocks were exposed for periods of up to 16 weeks at 25-27 degrees Celcius and 65-75% relative humidity. Efficacy was evaluated as mass loss on each block. This method is presented in E10-09 in the AWPA 2010 standards.

Results showed very small mass loss with MBE and creosote blends ranging from 2% to 10%. The blocks retained the majority of their pre-exposure weights as shown in Table 3. Losses are expected from the volatized of the creosote and these loss percentages are to be expected.

TABLE 3

Mass loss of soil blocks when subjected to AWPA E10-09.

| Fungi | Replications | Control % mass loss | Boron Ester/Creosote blends (mass loss %) 2% | 4% | 6% | 8% | 10% |
|---|---|---|---|---|---|---|---|
| 11245 | 7 | 60 | 7 | 4 | 6 | 4 | 4 |
| 12653 | 7 | 40 | 8 | 8 | 8 | 8 | 2 |
| 11538 | 7 | 40 | 6 | 6 | 5 | 6 | 5 |
| 32237 | 7 | 50 | 10 | 9 | 4 | 7 | 2 |
| 42462 | 7 | 60 | 6 | 8 | 6 | 4 | 4 |
| 11539 | 7 | 50 | 4 | 3 | 4 | 4 | 4 |

Example 6

MBE Additions do not Materially Affect the Properties of the Creosote Composition Experiments were undertaken to determine that the MBE additions did not materially affect the properties of the creosote composition as per the AWPA 2010 specification P1-P13-09 and P2-09. Table 4 shows the comparison of a 10% mixture which is the highest concentration ever used with creosote.

TABLE 4

P2-09 Standard for Creosote Composition Preservative Composition & Phys. Chem. Requirements of new material & material in use in treating composition.

| | New Material | | Material In Use | | Our Composition at MBE 10% (use) |
|---|---|---|---|---|---|
| Water Content (% by volume) | >1.5 | | >3.0 | | >1.5 |
| Material insoluble by Xylene | 3.5 | | >4 | | >3 |
| Specific Gravity @ 38° C. (compared to Water @15.5° C.) | | | | | |
| Whole Creosote | <1.080 | >1.130 | >1.080 | >1.130 | >1.095 |
| Fraction 235-315° C. | <1.025 | — | >1.025 | — | >1.025 |
| Fraction 315-355° C. | <1.085 | — | >1.085 | — | >1.093 |
| Distillation | | | | | |
| Up to 210° C. | — | <5.0 | — | <5.0 | <4.01 |
| Up to 235° C. | — | <25.0 | — | <25.0 | <23.5 |
| Up to 315° C. | >32.0 | — | >32.0 | — | <34.6 |
| Up to 355° C. | >52.0 | — | >52.0 | — | <54 |

Composition:
The material shall be a pure coal tar product derived entirely from tar produced by the carbonization of bituminous coal. It may either be a coal tar distillate or a solution of coal tar in coal tar distillate

Example 7

Optimization of Boron Penetration and Retention Using the Disclosed One-Step Creosote-Borate Treatment Process In order to optimize the boron penetration and retention during the one-step creosote-borate treatment process, operational parameters were varied to determine their effects in addition to variable percentages of MBE. The parameters tested were Boultonizing time and length of pressure cycle. The effect of variable preheating times had little to no effect on $B_2O_3$ retentions within the wood suggesting that a minimal preheat time of 4 hours was sufficient for borate retention. Pressure times were varied from 5 to 120 minutes, however, there was no apparent effect on borate retentions, indicating that borate diffusion occurs rapidly within the early stages of the treating cycle and is predominately influenced by temperature. Moisture content improved the rate of diffusion allowing wet charges to be treated easily. All data in Table 5 was full scale.

Figure 3:
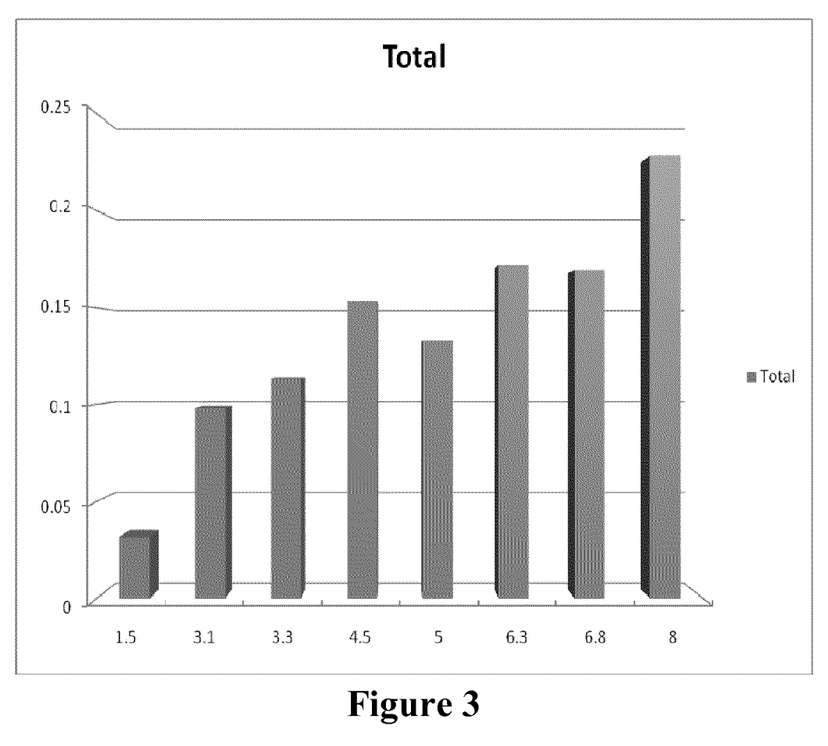
FIG. 3 is a bar graph showing the effect of increasing the concentration of monoethanolamine borate in the treatment composition in percent on $B_2O_3$ Retention in oak in pcf (parts per cubic foot).

The percentage MBE within the treating composition appears to have a linear effect on borate retention within both MHW and Oak. However, both the MHW and Oak retention data showed a maximum retention of approximately 0.15 pcf $B_2O_3$ occurring with MBE percentages ranging from 3-6.3. An increase to the retention of borate above 0.17 to 0.23 pcf, required an MBE percentage increase above 6.3%. Once above 6.3%, the borate retention to MBE % relationship was again that of an increasing linear trend. Our target was 0.09 pcf $B_2O_3$ or BAE. This was easily exceeded as shown in FIG. 3.

TABLE 5

Variable boltonizing/pressure times and the subsequent effect on $B_2O_3$ retentions.

| Species | MBE (%) | Boultinizing Time (Hr) | Pressure Time (Min) | $B_2O_3$ Retention PCF (Average) |
|---|---|---|---|---|
| MHW | 4.5 | 4 | 5 | 0.156 |
| Oak | 4.5 | 4 | 5 | 0.161 |
| MHW | 6.3 | 4.5 | 20 | 0.164 |
| Oak | 6.3 | 4.5 | 20 | 0.158 |
| MHW | 3.1 | 4.5 | 75 | 0.151 |
| Oak | 3.1 | 4.5 | 75 | 0.047 |
| MHW | 6.3 | 4.5 | 75 | 0.172 |
| Oak | 6.3 | 4.5 | 75 | 0.164 |
| MHW | 6.8 | 5 | 5 | 0.108 |
| Oak | 6.8 | 5 | 5 | 0.184 |
| MHW | 8.0 | 5.5 | 30 | 0.222 |
| Oak | 8.0 | 5.5 | 30 | 0.239 |
| MHW | 3.3 | 5.5 | 75 | 0.099 |
| Oak | 3.3 | 5.5 | 75 | 0.093 |
| MHW | 1.5 | 5.5 | 60 | 0.031 |
| Oak | 1.5 | 5.5 | 60 | 0.035 |
| MHW | 1.5 | 5.5 | 30 | 0.030 |
| Oak | 1.5 | 5.5 | 30 | 0.026 |
| MHW | 5.0 | 5.5 | 5 | 0.091 |
| Oak | 5.0 | 5.5 | 5 | 0.117 |
| MHW | 5.0 | 5.5 | 20 | 0.127 |
| Oak | 5.0 | 5.5 | 20 | 0.161 |
| MHW | 5.0 | 5.5 | 30 | 0.154 |
| Oak | 5.0 | 5.5 | 30 | 0.158 |
| MHW | 5.0 | 5.5 | 40 | 0.155 |
| Oak | 5.0 | 5.5 | 40 | 0.159 |
| MHW | 1.5 | 6.0 | 30 | 0.031 |
| Oak | 1.5 | 6.0 | 30 | 0.038 |
| MHW | 8 | 6.0 | 60 | 0.222 |
| Oak | 8 | 6.0 | 60 | 0.232 |
| MHW | 8 | 6.0 | 90 | 0.219 |
| Oak | 8 | 6.0 | 90 | 0.235 |
| MHW | 8 | 6.0 | 120 | 0.235 |
| Oak | 8 | 6.0 | 120 | 0.225 |

TABLE 6

MBE concentrations versus $B_2O_3$ Retentions no Boultonizing or Pressure Variations.

| Species | MBE (%) | $B_2O_3$ Retention PCF (Average) |
|---|---|---|
| MHW | 1.5 | 0.031 |
| Oak | 1.5 | 0.033 |
| MHW | 3.1 | 0.098 |
| Oak | 3.1 | 0.097 |
| MHW | 3.3 | 0.118 |
| Oak | 3.3 | 0.143 |
| MHW | 4.5 | 0.156 |
| Oak | 4.5 | 0.140 |
| MHW | 5 | 0.097 |
| Oak | 5 | 0.112 |
| MHW | 6.3 | 0.187 |
| Oak | 6.3 | 0.187 |
| MHW | 6.8 | 0.198 |
| Oak | 6.8 | 0.187 |
| MHW | 8 | 0.224 |
| Oak | 8 | 0.233 |

Example 8

The Disclosed One Step Process can be Applied to "Wet" Wood

The disclosed one step process was tested on "wet" wood. The wood was first treated to remove moisture. Wet wood was loaded into the cylinder or retort, which was then filled with the creosote and boron mixture. The temperature was then raised to around 200 F while pulling a vacuum to cause the water within the wood to be evaporated off to collection tanks Pressure is the time for the press and switch ties are pressed longer as they are larger in dimensions. Boultonizing preheat time is the time that the wood is boiled under vacuum to extract water. Specific conditions are provided in Table 7. The process was monitored to avoid the equalization of moisture that can cause the expulsion of preservative or bleeding. The amount of boron in the wood was then assessed and the results are shown in Table 7 below. In Table 6, "MHW" is mixed hardwood, $B_2O_3$ and DOT results are from a standard titration procedure. Retention is the pounds of creosote per cubic foot of wood.

TABLE 7

BORATE RESULTS—Wet Material.

| MATERIAL | | | CYCLE | | RETENTIONS | | | |
|---|---|---|---|---|---|---|---|---|
| | | | Preheat/ Boult | Pressure Time | % | $B_2O_3$ | Dot | Atomic Absorb. |
| Species | Pcs | Item | (Hours) | (Min) | B2O3 | (Lbs/Cuft) | (Lbs/Cuft) | (ppm) |
| MHW | 318 | 7" | 6 | 5 | 6.140 | 0.258 | 0.104 | 0.154 | 1470 |
| MHW | 318 | 7" | 5 | 5 | 6.054 | 0.332 | 0.134 | 0.198 | 922 |
| MHW | 318 | 7" | 5 | 5 | 3.546 | 0.221 | 0.099 | 0.154 | 892 |
| MHW | 318 | 7" | 5 | 5 | 6.227 | 0.258 | 0.108 | 0.158 | 1180 |
| OAK | 240 | SW* | 17 | 15 | 3.596 | 0.202 | 0.091 | 0.154 | 789 |
| OAK | 192 | SW* | 16 | 10 | 4.276 | 0.202 | 0.121 | 0.155 | 845 |
| | | | | | Req'd | | 0.090 | | |

*SW = Switch

Example 9

Wood Treated with the Disclosed One Step Process Retains the Ability to be Burned as a Fuel Source A burn test was conducted by the ICSET gas emissions laboratory in Bowling Green Ky., to compare the combustion of one step, two step and creosote only ties. This confirms that the addition of boron by the one step method does not impact the ability of the tie to be burned as a fuel source for electrical power.

Example 10

Wood Treated with DOT

DOT (or a 50/50 mixture of boric acid and DOT) were added to de-ionized water. MEA was added and the solution temperature increased with applied heat. More DOT (or 50/50 DOT and boric acid) was added to bring the concentration to 50% DOT (or 50/50 DOT and boric acid) in water. The final temperature for the reaction was above 170° F. and agitation was used to keep the DOT (or 50/50 DOT and boric acid) in solution.

To some batches, isopropyl alcohol (IPA) was added in a ratio of about 50% w/w IPA relative to the weight of DOT (or the weight of the 50/50 mixture of boric acid and DOT) in the composition. Some batches were made with IPA added in a ratio of about 50% w/w relative to the weight of boric acid in the composition.

What is claimed is:

1. A method of treating wood, comprising the steps of:
   a) immersing the wood in a treatment solution; and
   b) exposing the immersed wood from step (a) to conditions which cause boron to migrate into the interior of the wood;
   wherein the treatment solution comprises (1) at least about 3% w/w of a reaction product of alkanolamine and borate; wherein the reaction product comprises an alkanolamine ester of the borate; and (2) at least about 90% w/w creosote;
   wherein the borate comprises disodium octaborate tetrahydrate (DOT); and the treatment solution is greater than 98% free of water and is a homogeneously mixed blend.

2. The method of claim 1, wherein the alkanolamine comprises a $C_2$-$C_6$ monoalkanolamine.

3. The method of claim 1, wherein the alkanolamine comprises monoethanolamine.

4. The method of claim 1, wherein the composition comprises at least about 95% w/w creosote.

5. The method of claim 1, wherein the creosote comprises heavy bunker C fuel oil.

6. The method of claim 1, wherein the creosote comprises about 40 to 60% w/w heavy bunker C fuel oil.

7. The method of claim 1, wherein at least about 40% w/w of the borate is disodium octaborate tetrahydrate (DOT).

8. The method of claim 1, wherein the borate comprises disodium octaborate tetrahydrate (DOT) and boric acid.

9. The method of claim 1, wherein the reaction product comprises unreacted borate.

10. The method of claim 1, wherein the treatment solution further comprises biodiesel.

11. The method of claim 1, wherein exposing the immersed wood to conditions which cause boron to migrate into the interior of the wood comprises pressure impregnation of the wood with the treatment solution.

12. The method of claim 11, wherein the pressure impregnation operation comprises exposing the immersed wood to a temperature of between 160-240° F. and a pressure of 100-160 pounds per square inch (psi).

13. The method of claim 11, wherein the pressure impregnation results in the wood having of boron content of at least about 0.11 pounds per cubic foot (pcf) Boric Acid Equivalent (BAE).

14. The method of claim 11, wherein the pressure impregnation comprises exposing the immersed wood to a temperature of 190-210° F. and a pressure of 130-160 psi for 20 minutes to 5 hours.

15. The method of claim 1, further comprising c) separating the treated wood from the treatment solution after the pressure impregnation; d) exposing the treated wood to an expansion bath; e) exposing the treated wood to a vacuum treatment after completion of the expansion bath.

16. The method of claim 1, wherein the conditions which cause boron to migrate into the interior of the wood result in the wood having of boron content of at least about 0.05 pcf BAE.

17. The method of claim 1, wherein the creosote comprises heavy bunker C fuel oil; the alkanolamine comprises monoethanolamine; and the borate comprises disodium octaborate tetrahydrate.

18. The method of claim 17, wherein the treatment solution further comprises biodiesel.

19. The method of claim 1, wherein the treatment solution has a specific gravity @ 38° C. of at least 1.08 (compared to water @ 15.5° C.).

20. The method of claim 1, wherein the treatment solution comprises least about 95% w/w creosote; the creosote comprises about 40 to 60% w/w heavy bunker C fuel oil; at least about 40% w/w of the borate is disodium octaborate tetrahydrate (DOT); and the treatment solution further comprises biodiesel.

21. A method of treating wood, comprising the steps of:
pressure impregnation of wood immersed in a preservative solution at 160-240° F. and a pressure of 100-160 pounds per square inch (psi);
wherein the preservative solution comprises (1) at least about 90% w/w creosote;
and (2) at least about 3% w/w of a reaction product of alkanolamine and borate, which comprises an alkanolamine ester of the borate;
the borate includes boric acid and at least about 40% w/w of the borate is disodium octaborate tetrahydrate (DOT);
wherein the preservative solution is greater than 98% free of water and is a homogeneously mixed blend.

* * * * *